United States Patent [19]

Miyake

[11] 4,219,571

[45] Aug. 26, 1980

[54] PROCESS FOR PRODUCING A SWEETENER

[75] Inventor: Toshio Miyake, Okayama, Japan

[73] Assignee: Kabushiki Kaisha Hayashibara Seibutsu Kagaku Kenkyujo, Okayama, Japan

[21] Appl. No.: 915,876

[22] Filed: Jun. 15, 1978

[51] Int. Cl.$^2$ ............................................. A23L 1/236
[52] U.S. Cl. ......................................... 426/48; 426/52; 426/658; 426/804; 435/78; 435/96; 435/97; 435/99
[58] Field of Search ................. 426/48, 658, 548, 804, 426/661, 49, 52; 195/31 R; 435/78, 96, 97, 99

[56] References Cited

U.S. PATENT DOCUMENTS

| | | | |
|---|---|---|---|
| 2,742,365 | 4/1956 | Corman et al. | 426/48 |
| 3,819,484 | 6/1974 | Okada et al. | 195/31 R |
| 4,082,858 | 4/1978 | Morita et al. | 426/658 X |

OTHER PUBLICATIONS

Kohda et al., *Phytochemistry*, 15, (1976), 981–983.

*Primary Examiner*—Esther M. Kepplinger
*Attorney, Agent, or Firm*—Browdy and Neimark

[57] ABSTRACT

A sweetener containing alpha-glycosyl stevioside which is obtained by allowing alpha-glucosyltransferase to react on an aqueous solution containing stevioside and alpha-glucosyl sugar compound.

5 Claims, 4 Drawing Figures

PROCESS FOR PRODUCING A SWEETENER

DETAILED DESCRIPTION OF THE INVENTION

Figure 1:
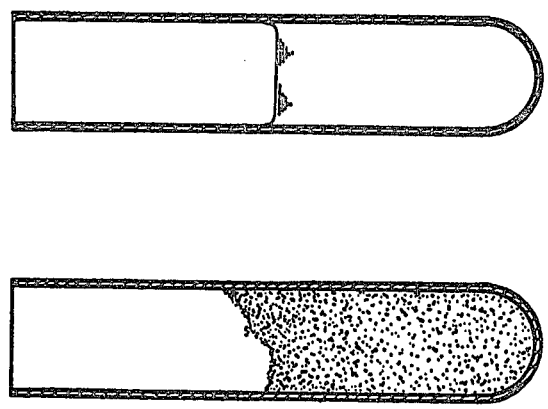

The present invention relates to a process for producing a sweetener, characterized in allowing alpha-glucosyltransferase to act, during the production of the sweetener, on an aqueous solution containing stevioside and alpha-glucosyl sugar compound to form alpha-glycosyl stevioside and to obtain the alpha-glycosyl stevioside or an alpha-glycosyl stevioside containing sweetener.

Recently, because the use of artificial sweetener such as dulcin, sodium cyclamate and saccharin has been banned or restricted, in view of the foods sanitation, harmless natural sweeteners are receiving ever-increasing demands. In response to the demands, a rage for production increase of stevioside is rapidly amounting among the agriculturally-concerned, and sweetener manufacturers.

Stevioside is a naturally-occuring glycoside obtained by extracting the overground portion, e.g., leaves and stems, of Stevia rebaudiana BERTONI (hereinafter referred to as Stevia), a member of the Chrysanthemum family. The glycoside is, as shown in the formula, a beta-glucosyl glycoside wherein the aglycon is steviol.

Chemical Structure of Stevioside

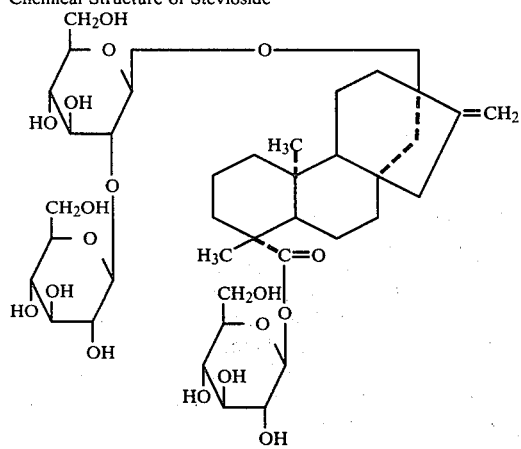

Stevioside, in extract of Stevia leaves, in crude and refined form or in mixtures with other sweeteners, is used as sweetener to sweeten foods and drinks.

As well-known, the uses of stevioside or conventional stevioside-containing sweetener, are restricted, require special precautions or render difficulties due to their following inherent disadvantages and properties.

1. Besides being sweet, stevioside imparts bitterness and astringency.
2. The sweetness of stevioside effects slower in the mouth than that of sucrose and gives a lingering, unpleasant aftertaste.
3. Stevioside is difficultly soluble in water; its solubility being only 0.12% at 20° C.

The present inventor performed painstaking research and development with the purpose to eliminate or solve the problems by biochemical means.

The efforts resulted in the invention of a process wherein the subjection of an aqueous solution containing stevioside and one or more alpha-glucosyl sugar compounds selected from the group comprising maltooligosaccharides such as maltose, maltotriose, maltotetraose, partial hydrolyzates of starch, and sugar compounds containing alpha-glucosyl residue such as sucrose, to the action(s) of alpha-glucosyltransferase(s), which is capable of transferring alpha-glucosyl residue to stevioside, e.g., alpha-glucosidase (E.C.3.2.1.20), alpha-amylase (E.C.3.2.1.1), cyclodextrin glucanotransferase (E.C.2.4.1.19), and dextran sucrase (E.C.2.4.1.5), yields sweetener containing the alpha-glycosyl stevioside formed by the reaction and possessing the following outstanding desirable properties and features that are unattainable with conventional stevioside products or stevioside containing sweeteners.

More particularly, the new sweetener

1. Possesses neither bitterness nor astringency, imparts a mild, soft, round and pleasant sweetness,
2. Without a lingering taste, and
3. Possesses a substantially and desirably improved water solubility.

In addition, the inventor confirmed by thin-layer chromatography that the reaction converts a portion or nearly all of the stevioside used in the reaction into alpha-glycosyl stevioside, such as alpha-monoglucosyl stevioside, alpha-diglucosyl stevioside and alpha-triglucosyl stevioside.

Recently, new substances called rebaudioside A and rebaudioside B which are entirely different from stevioside were found in the leaves of Stevia. As apparent from the following formulae, rebaudioside A and rebaudioside B are a beta-glucosyl glycoside wherein the aglycon is steviol as in the case of stevioside.

Chemical Structure of Rebaudioside A

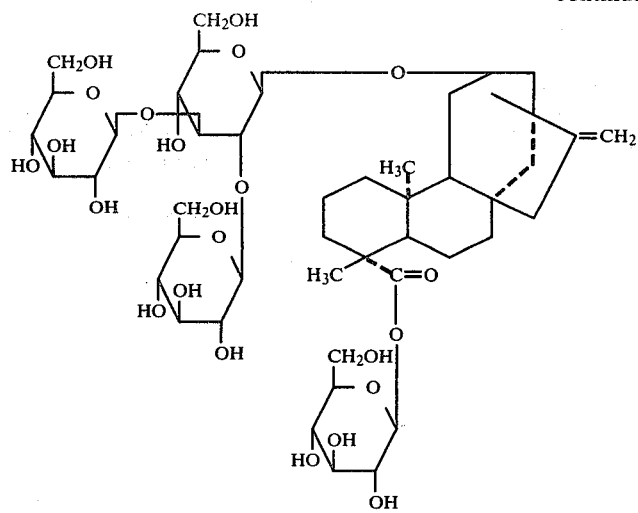

Chemical Structure of Rebaudioside B

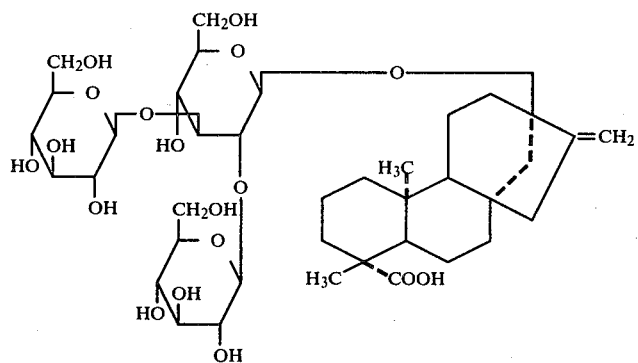

Whereas the alpha-glycosyl stevioside present in the sweetener according to the invention is decomposed by alpha-glucosidic linkage-hydrolyzing enzymes, e.g., glucoamylase, alpha-glucosidase, beta-amylase and isomaltodextranase, into stevioside, D-glucose, maltose or isomaltose, rebaudioside A and B (hereinafter referred to as rebaudiosides unless otherwise specified) were confirmed as undecomposable by such alpha-glucosidic linkage hydrolyzing enzymes. Moreover, the subjection of an aqueous solution containing alpha-glucosyl sugar compound and rebaudiosides to alpha-glucosyltransferase does not decompose rebaudiosides but forms alpha-glycosyl rebaudiosides similarly as in the previously described case of allowing the enzyme to act on stevioside. The resulting reaction mixture also possesses a similarly mild, soft, round and pleasant sweetness which is substantially superior to the unreaction mixture in quality. Accordingly, the alpha-glycosyl stevioside obtained by the present invention is apparently distinguishable from the conventionally-known stevioside or rebaudiosides.

The stevioside which is used to form the sweetener according to the present invention in the presence of alpha-glucosyl sugar compound is not necessarily limited to highly refined or purified stevioside products, but may be a mixture of stevioside and rebaudiosides, or a crude stevioside product or even a stevioside by-product containing impurities, e.g., mother liquor containing still a large amount of stevioside and rebaudiosides obtained by extraction of Stevia and from which crystalline stevioside has been removed.

The alpha-glucosyl sugar compound employable in the invention may be one that forms alpha-glycosyl stevioside from stevioside when both are subjected to the action of the alpha-glucosyltransferase. Accordingly, substrates which favour action of alpha-glucosyltransferase, namely alpha-glucosyl sugar compounds such as a partial starch hydrolyzate, sucrose and the likes, are chosen. For example, alpha-glucosyl sugar compounds such as maltooligosaccharide, e.g., maltose, maltotriose, maltotetraose, a partial starch hydrolyzate with a dextrose equivalent (hereinafter abbreviated as D.E.) from about 10 to about 70 and sucrose are suitable substrates for alpha-glucosidase (E.C.3.2.1.20) when used as alpha-glucosyltransferase; alpha-glucosyl sugar compounds ranging from gelatinized starch product with D.E. not higher than 1 to a partial starch hydrolyzate (maltodextrin) with D.E. of about 30 for alpha-amylase (E.C.3.2.1.1); a cyclodextrin or alpha-glucosyl sugar compounds ranging from a gelatinized starch product with D.E. of not higher than 1 to a partial starch hydrolyzate with D.E. of about 60 for cyclodextrin glucanotransferase (E.C.2.4.1.19); and sucrose of dextransucrase (E.C.2.4.1.5).

Of the employable alpha-glucosyl sugar compounds in the invention, the gelatinized starch product or partial starch hydrolyzate may be a product obtained from cereal starch, e.g., wheat starch and corn starch, tuber- and root-starch, e.g., sweet potato starch, potato starch and tapioca starch.

The gelatinized starch product is prepared by gelatinization attained by heating a starch slurry to a temperature above the gelatinization point, generally from 70° C. to 140° C. The partial starch hydrolyzate is obtained by hydrolyzing a starch slurry with acid(s) and/or amylase(s) to the desired D.E. In the invention, the alpha-glucosyl sugar compound may be of one type, or more than one type may be used concurrently.

Any alpha-glucosyltransferase may be freely chosen for the invention as far as it forms alpha-glycosyl stevioside without decomposing stevioside when allowed to act on an aqueous solution containing alpha-glucosyl sugar compound (a suitable substrate for the enzyme) and stevioside.

Employable alpha-glucosyltransferase that yields favourable results include, for example, alpha-glucosidase (E.C.3.2.1.20) derived from animal sources such as pig liver, plant sources, such as buck wheat seed, fungi such as those of genera Mucor and Penicillium, yeasts such as those of genus Saccharomyces; alpha-amylase (E.C.3.2.1.1) derived from various microorganisms, especially bacteria of genus Bacillus, and from fungi of genus Aspergillus; cyclodextrin glucanotransferase (E.C.2.4.1.19) derived from various microorganisms, especially bacteria of genus Bacillus, and genus Klebsiella; dextran sucrase (E.C.2.4.1.5) derived from bacteria of genus Leuconostoc; dextrin dextranase (E.C.2.4.1.2) derived from bacteria of genus Acetobacter; amylosucrase (E.C.2.4.1.4) derived from bacteria of genus Neisseria.

Purification of the alpha-glucosyltransferase is not necessarily required as far as the above described conditions are satisfied and usually the objectives of the invention are attainable with a crude alpha-glucosyltransferase.

For example, a crude alpha-glucosyltransferase of animal and plant origins is obtained by salting-out an extraction solution of ground or minced animal or plant tissues with ammonium sulfate, or by precipitating and separating the extraction solution with organic precipitants such as alcohol or acetone so as to attain the objectives of the invention. If necessary, the crude transferase may be purified by any known method before its use.

Known microbial alpha-glucosyltransferase includes those derived from bacteria, fungi, yeasts and other microorganisms. Usually, the solid culture method used for "koji" and the liquid culture method such as the tank culture method are used for the production of such transferase. Similarly as in the case of transferase of animal and plant origins, microbial alpha-glucosyltransferase is prepared by extraction and, if necessary, may be purified prior to their use by any known method.

Although in the case of liquid culture and culture broth intact may be used as alpha-glucosyltransferase, usually the supernatant from which insolubles are removed is used as alpha-glucosyltransferase. Alternatively, the elaborated enzyme may be utilized in the form of cells or after extracting the enzyme from the cells and, if necessary, may be purified further prior to its use.

Commercialized alpha-glucosyltransferase is also employable.

Alpha-glucosyltransferase can be immobilized on suitable supports and the immobilized enzyme may be used repeatedly in batchwise system or continuous system. The sweetener of the invention can be prepared by cultivating alpha-glucosyltransferase-producing microorganism, animal tissue or plant tissue in a medium containing alpha-glucosyl sugar compound and stevioside to form alpha-glucosyl stevioside.

The reaction condition of the invention is such that allows alpha-glucosyltransferase to act on an aqueous solution containing stevioside and alpha-glucosyl sugar compound.

The aqueous solution that contains stevioside and alpha-glucosyl sugar compound is prepared by heating to dissolve stevioside and is brought to give a stevioside concentration of about 0.1 to about 20% (w/w) and an alpha-glucosyl sugar compound concentration of about 1 to about 50% (w/w). The preferable ratio of alpha-glucosyl sugar compound against stevioside ranges from about 0.5 to about 500 times, d.s.b.

The pH and temperature of the reaction solution should be in the ranges that effect formation of alpha-glycosyl stevioside by the action of alpha-glucosyltransferase(s), usually pH 3–10 and 20°–80° C. are chosen. In the reaction, the amount of enzyme used is closely related to the reaction duration. Therefore, from economic point of view, usually, an amount of enzyme sufficient to complete the reaction in about 5–80 hours is chosen.

The reaction solution in which alpha-glycosyl stevioside is thus formed can be used intact as sweetener. If desirous, the reaction solution is heated to inactivate the enzyme, filtrated, desalted by passage of the filtrate through ion exchange resins, e.g., H type strongly acidic ion exchange resin and OH type weakly basic ion exchange resin, and concentrated into a syrup sweetener, or the concentrate may be dried and pulverized to yield a powder sweetener. Any known method in the art for concentration, drying and pulverizing, e.g., vacuum evaporation, vacuum drying and spray drying, may be used. The sweetness of the resulting alpha-glycosyl stevioside-containing sweetener is generally, roughly equal to or slightly weaker than the sweetness in which stevioside of the same solid weight is used for the reaction imparts. Moreover, the sweetness of the new sweetener is mild, soft, round and pleasant, hardly imparting bitterness or astringency, and has no lingering taste.

The formed alpha-glycosyl stevioside and unreacted stevioside present in the syrup sweetener of the invention do not crystallize on prolonged storage. The new powder sweetener of the invention is a so-called powder solid solution wherein the formed alpha-glycosyl stevioside, unreacted stevioside, reacted and unreacted-alpha-glucosyl sugar compounds are mutually dissolved. Accordingly, the water solubility of the powder sweetener is so high that it will dissolve instantly with no limitation; it dissolves freely even at high concentration to form syrup or paste.

As described above, the sweetener of the invention is different from conventional stevioside products or simple mixtures comprising stevioside and other sweeteners in that it dissolves freely without requiring heating due to its extremely higher solubility. As will be described in details, the feature can be utilized with outstanding results when used to sweeten powder form instant foods, first foods, convenient foods and ingredients thereof.

The sweetener of the invention may be used intact as seasoning to sweeten foods and drinks. If preferable, the sweetener may be admixed with other sweeteners, e.g., starch syrups, glucose, maltose, isomerized sugar, sucrose, honey, maple sugar, sorbit, maltitol, dihydrochalcone, L-aspartyl L-phenylalanine methyl ester, saccharin, alanine and glycyrrhizin, fillers, e.g., dextrins, starch and lactose, flavouring agents, and coloring agents.

Among the sweetener products of the invention, powder products may be used intact or molded into granular, spherical and tablet forms after adding suitable fillers and excipients, while in the case of syrup product the concentration can be adjusted to meet the final use, and the syrup can be packed in container or vessel of any shape.

Since, as described above, the sweetness of the sweetener of the invention is roughly equal to or slightly weaker than the sweetness that stevioside of the same solid weight used for the reaction imparts, the sweetness varies with the ratio of stevioside to alpha-glucosyl sugar compound used in the reaction. The sweetness attained with using a stevioside to alpha-glucosyl sugar compound ratio of about 1:50–100 is generally equal to that of sucrose, d.s.b.

If the ratio exceeds about 100 and especially when gelatinized starch, partial starch hydrolyzate or maltooligosaccharide is used as alpha-glucosyl sugar compound, the resulting sweetness will be weaker than that of sucrose, d.s.b. Accordingly, such sweetener can be used as a sweetener which imparts desirable texture such as thickness, viscosity, consistency, weight or body to foods, drinks, confectioneries and pharmaceuticals and which reduces the sweetness in the final products.

On the other hand, if the ratio is brought down to lower than about 50 times, the sweetness of the new sweetener will be, generally, higher than that of sucrose, d.s.b., and the sweetness intensifies inversely proportionally with the decline of the ratio. Removal of the alpha-glucosyl sugar compound portion from the sweetener prepared in accordance with the invention will increase the sweetness of the sweetener to about 50–100 times of that of sucrose. Further the employment of such sweetness-intensified sweetener for sweetened foods, drinks and confectioneries will lower their caloric values since a substantially less amount of the sweetener is required to obtain the sweetness realized with sucrose. In other words, the new sweetener of the invention can be used as a low-caloric dietary sweetener for the obeses, the diabetics and those whose caloric intakes are restricted as well as for sweetening low caloric dietary foods, drinks and confectioneries, i.e., the so-called beauty diets, health diets and other diets.

Moreover, the sweetener of the invention can also be used as a low-cariogenic or low-dental caries inducing sweetener since it is difficultly fermentable by cariogenic microorganisms. Embodiments are low cariogenic foods and drinks including confectioneries such as chewing gums, chocolates, biscuits, cookies, caramels, toffees and candies; soft drinks such as colas, juices, coffee, tea and lactic-acid beverages; alcoholic beverages; as well as dentifrices, gargles and pharmaceuticals aimed at the same objectives.

Since the sweetener of the invention is compatible with and harmonize well and desirably with food ingredients or additives which have other taste sensories such as sourness, saltness, astringency, bitterness and palatability to improve the taste and quality of the final products, and is highly acid- and thermal-resistant, it may be used freely in foods, drinks and confectioneries, besides the above described products, in general, giving favourable results and improving their palatability.

Furthermore, the sweetener may be used as a palatability improver for feeds directed to domestic animals, cattles, horses, poultry, fish, honey bees, silk worms and others.

The sweetener may be also used for sweetening various products of tobacco, products confectioneries, cosmetics and pharmaceuticals of various forms (in solid, paste, liquid) such as lipcream, lipstick, dentifrice, mouth refresher, gargles, bad-breath-remover tablet, troche, sugar coating drops of cod-liver oil, medicine of oral administration, or freely used as gustatory improving agent, taste improver.

On employing the sweetener of the invention in the above described foods, drinks, confectioneries, feed, cosmetics or dentrifies, and pharmaceuticals, any known method in the art may be chosen, for example, mixing, kneading, dissolving, dipping or immersing, permeance, dispersing, coating, spraying, infusing, etc.

The sweetener will be described with reference to the following experiments.

EXPERIMENT 1.

Preparation of Sweetener 1-(1) Preparation of alpha-glucosyltransferase

A strain of *Bacillus stearothermophilus* FERM-P No. 2222 was inoculated on 10 liters of a sterilized culture medium containing 2% (w/v) soluble starch, 1% (w/v) ammonium nitrate, 0.1% (w/v) dipotassium hydrogen phosphate, 0.05% (w/v) magnesium sulfate $7H_2O$, 0.5% (w/v) corn steep liquor, and 1% (w/v) calcium carbonate, and the mixture was incubated at a temperature of 50° C. for three days with aeration and stirring. The resultant culture broth was centrifuged and the supernatant was salted-out with 0.7 saturation ammonium sulfate, whereby a crude enzyme preparation with an activity of about 80,000 units was obtained. The enzymatic activity is assayed as follows. A mixture prepared by adding 0.2 ml of an enzyme solution to 5 ml of a solution containing 0.3 g/dl soluble starch, 0.02 M acetate buffer, pH 5.5 and $10^{-3}$ M $CaCl_2$ was allowed to react at 40° C. for 10 minutes. A 0.5 ml aliquot of the reaction mixture was collected, poured into 15 ml of 0.02 N $H_2SO_4$ to terminate the reaction and assayed on optical density at 660 nm after addition of 0.2 ml of 0.1 N $I_2$-KI solution. One unit of activity was designated as the amount of enzyme that caused disappearance of iodine stain in 15 mg soluble starch at 40° C. within 10 minutes.

1-(2) Reaction

"Commercialized stevioside", Stevia Sugar (Morita Kagaku Kogyo Co., Ltd., Osaka, Japan), 200 g, consisting of roughly equal amounts of purified stevioside and lactose, hereinafter referred to as "commercialized stevioside" and maltodextrin, D.E.30, 1000 g, were dissolved with heating in 3,000 ml of water. After cooling to 60° C. the solution was added 1,000 units of crude cyclodextrin glucanotransferase obtained in Experiment 1-(1), adjusted to pH 6.0 and allowed incubation at a temperature of 60° C. for 40 hours. After holding the reaction solution at a temperature of 95° C. for 10 minutes to inactivate the enzyme by heating (the preparation corresponds to Sample No. 3 in Table 1), the filtrate obtained by filtration was decolorized with a little amount of activated carbon and then desalted by passage through ion exchange resins, Amberlite IR-200C (H Type) and Amberlite IRA-93 (OH Type) (Rohm & Haas Co., Philadelphia, U.S.A.) at SV 2. Subsequently, the solution was concentrated at a temperature of 70° C. or below under reduced pressure and dried into powder forms (the preparation corresponds to Sample No. 4 in Table 1). The controls were obtained by similar processes following dissolution by heating such as the reaction process and inactivation process by heating, the starting material of the controls are given in Table 1.

7% sucrose solution were approximately equal in sweetness.

Similarly, Sample No. 2 and the 7% sucrose solution were rated approximately equally sweet based on the "sweeter" to "less sweet" ratio. Accordingly the sweetening power of Sample No. 1 was concluded as corresponding to the 7% sucrose solution. Similarly, the Table 1

| Sample | No. 1 (control) | No. 2 (control) | No. 3 (product of the invention) | No. 4 (product of the invention) |
|---|---|---|---|---|
| Starting material | 200 g "commercialized stevioside" | 200 g "commercialized stevioside" + 1,000 g maltodextrin + 1,000 units enzyme preinactivated by heating | 200 g "commercialized stevioside" + 1,000 g maltodextrin + 1,000 units enzyme | 200 g "commercialized stevioside" + 1,000 g maltodextrin + 1,000 units enzyme |
| Remarks | prepared similarly as Sample No. 3 | prepared similarly as Sample No. 3 | crude liquid sweetener obtained by heating | powder sweetener prepared by purifying and drying Sample No. 3 |

EXPERIMENT 2

Taste Tests 2-(1) Comparison of Sweetness

The concentration of every taste test solution was adjusted in reference to the preliminary test results to approximate the sweetness. More particularly, the concentration of the controls was adjusted to give a "commercialized stevioside" concentration of 0.13 % (w/v), while the concentration for the sweetener of the invention was adjusted to correspond to a concentration of 0.20% (w/v) of "commercialized stevioside".

The test panel member gave their sweetness sensory results in reference to a sucrose (granulated sugar) solution of a certain concentration, stating whether they found the test solution sweeter or less sweet than the sucrose solution. The tests were performed with a panel of 20 members at room temperature. The results are listed in Table 2.

sweetening power of Sample No. 3 was determined as corresponding to that of the 10% sucrose solution, and Sample No. 4 to the 9% sucrose solution.

Accordingly, no differences were noted between the sweetening powers of Samples No. 1 and No. 2 based on the amount of "commercialized stevioside" used in both Samples, d.s.b., and the sweetening power was calculated as about 53 times of that of sucrose. Samples No. 3 and No. 4 were also calculated as having sweetening powers of 50 and 45 times respectively of that of sucrose, while they were roughly equal to or slightly lower than those of Samples No. 1 and No. 2. In other words, the sweetening powers of the sweetener prepared in accordance with the invention are approximately equal to or slightly lower than that of stevioside in the amount used as material.

2-(2) Comparison Tests of Sweetness Quality

Comparison tests were performed with controls (Samples No. 1 and No. 2) and sweeteners of the inven- Table 2

| Sample Comparison of sweetness | No. 1 (control) | | | No. 2 (control) | | | No. 3 (product of the invention) | | | No. 4 (product of the invention) | | |
|---|---|---|---|---|---|---|---|---|---|---|---|---|
| Sucrose concentration % (w/w) | sweeter | same | less sweet | sweeter | same | less sweet | sweeter | same | less sweet | sweeter | same | less sweet |
| 6 | 13 | 5 | 2 | 15 | 3 | 2 | / | / | / | / | / | / |
| 7 | 10 | 2 | 8 | 8 | 5 | 7 | / | / | / | 20 | 0 | 0 |
| 8 | 4 | 4 | 12 | 3 | 3 | 14 | 16 | 2 | 2 | 15 | 4 | 1 |
| 9 | 1 | 3 | 16 | 1 | 2 | 17 | 10 | 5 | 5 | 8 | 6 | 6 |
| 10 | 0 | 2 | 18 | 0 | 1 | 19 | 7 | 4 | 9 | 0 | 6 | 14 |
| 11 | / | / | / | / | / | / | 2 | 3 | 15 | 0 | 6 | 14 |
| 12 | / | / | / | / | / | / | 0 | 2 | 18 | 0 | 2 | 18 |

Note: Figures indicate number of answers

As the results shown in Table 2 indicate, the respective ratios of those who answered Sample No. 1 "sweeter" than the 6% and 7% sucrose solutions to those who answered "less sweet" were 13:2 and 10:8, whereas the ratios were 4:12 and 1:16 in comparison with the 8% and 9% sucrose solutions. Based on the close ratio it was concluded that Sample No. 1 and the tion (Samples No. 3 and No. 4) on their sweetness quality.

Aqueous solutions of the above Samples were prepared to give a sweetness corresponding respectively to those of the 5%, 10% and 15% aqueous sucrose solutions by calculation on the basis of the result of the Experiment 2-(1). The test panel of 20 members were instructed to choose at room temperature among the test aqueous solutions of Samples No. 1-4 the respective samples with the most desirable and the most undesirable sweetness quality. The results are listed in Table 3.

Sample No. 4 which was obtained by purifying, concentrating and drying Sample No. 3 was a so-called "solid solution" wherein constituents such as alpha- Table 3

| Sample Sweetness | No. 1 (control) | | No. 2 (control) | | No. 3 (product of the invention) | | No. 4 (product of the invention) | |
|---|---|---|---|---|---|---|---|---|
| quality Sweetness | most desirable | most undesirable | most desirable | most undesirable | most desirable | most undesirable | most desirable | most undesirable |
| 5% sucrose solution | 0 | 10 | 0 | 10 | 4 | 0 | 16 | 0 |
| 10% sucrose solution | 0 | 8 | 0 | 12 | 6 | 0 | 14 | 0 |
| 15% sucrose solution | 0 | 11 | 0 | 9 | 7 | 0 | 13 | 0 |

Note: Figures indicate number of answers

As apparent from the results in Table 3, the sweetness qualities of the controls, Samples No. 1 and No. 2, were rated as most inferior at every degree of sweetness, thus no differences were noted between Samples No. 1 and No. 2, whereas it is clear that the sweetness qualities of Samples No. 3 and No. 4 were superior at every degree of sweetness. Especially the further purified sweetener, Sample No. 4 was observed as being slightly superior to Sample No. 3 in sweetness quality. The responses from the panel members on sweetness quality are listed in Table 4.

glycosyl stevioside, stevioside, alpha-glucosyl sugar compounds were mutually dissolved and the solubility was so high that it instantly dissolved in water and that even at high concentration it freely dissolved to form into paste.

EXPERIMENT 4

Identification of Alpha-glycosyl Stevioside

Five grams of Sample No. 4 obtained in Experiment 1-(2) was added to a solvent system of water-saturated n-butanol 200 ml and water 200 ml placed in a separat- Table 4

| Sample Corresponding sweetness | No. 1 (control) | No. 2 (control) | No. 3 (product of the invention) | No. 4 (product of the invention) |
|---|---|---|---|---|
| 5% sucrose solution | Sweet, bitter, astringent, no lingering after taste, difficult to use intact | Sweet, bitter, astringent, no lingering after taste, difficult to use intact | Sweet, light, soft, round, pleasant, similar to sucrose, no lingering after taste, advantageously intact may be used | Sweet, soft, round, pleasant, similar to sucrose, no lingering after taste, advantageously intact may be used |
| 10% sucrose solution | Sweet, sharp, stimulant, strong bitter, astringent, no lingering after taste, difficult to use intact | Sweet, sharp, stimulant, strong bitter, astringent, no lingering after taste, difficult to use intact | Sweet, soft, round, pleasant, similar to sucrose, no lingering after taste, advantageously intact may by used | Sweet, soft, round, pleasant, similar to sucrose, no lingering after taste, advantageously intact may be used |
| 15% sucrose solution | Sweet, sharp, stimulant, bitter, astringent, no lingering after taste, difficult to use intact | Sweet, sharp, stimulant, bitter, astringent, no lingering after taste, difficult to use intact | Sweet, soft, round, pleasant, similar to sucrose, no lingering after taste, advantageously intact may be used | Sweet, soft, round, pleasant, similar to sucrose, no lingering after taste, advantageously intact may be used |

As the above test results apparently show, unlike the conventional stevioside or mixture of stevioside and other sweeteners, the sweetener of the invention have a mild, soft, round and pleasant sweetness closely resembling that of sucrose without an undesirable lingering after-taste, and are superlative sweeteners which impart to the mouth directly a pleasant and enjoyable sweetness.

EXPERIMENT 3

Comparison of Solubility

Figure 2:
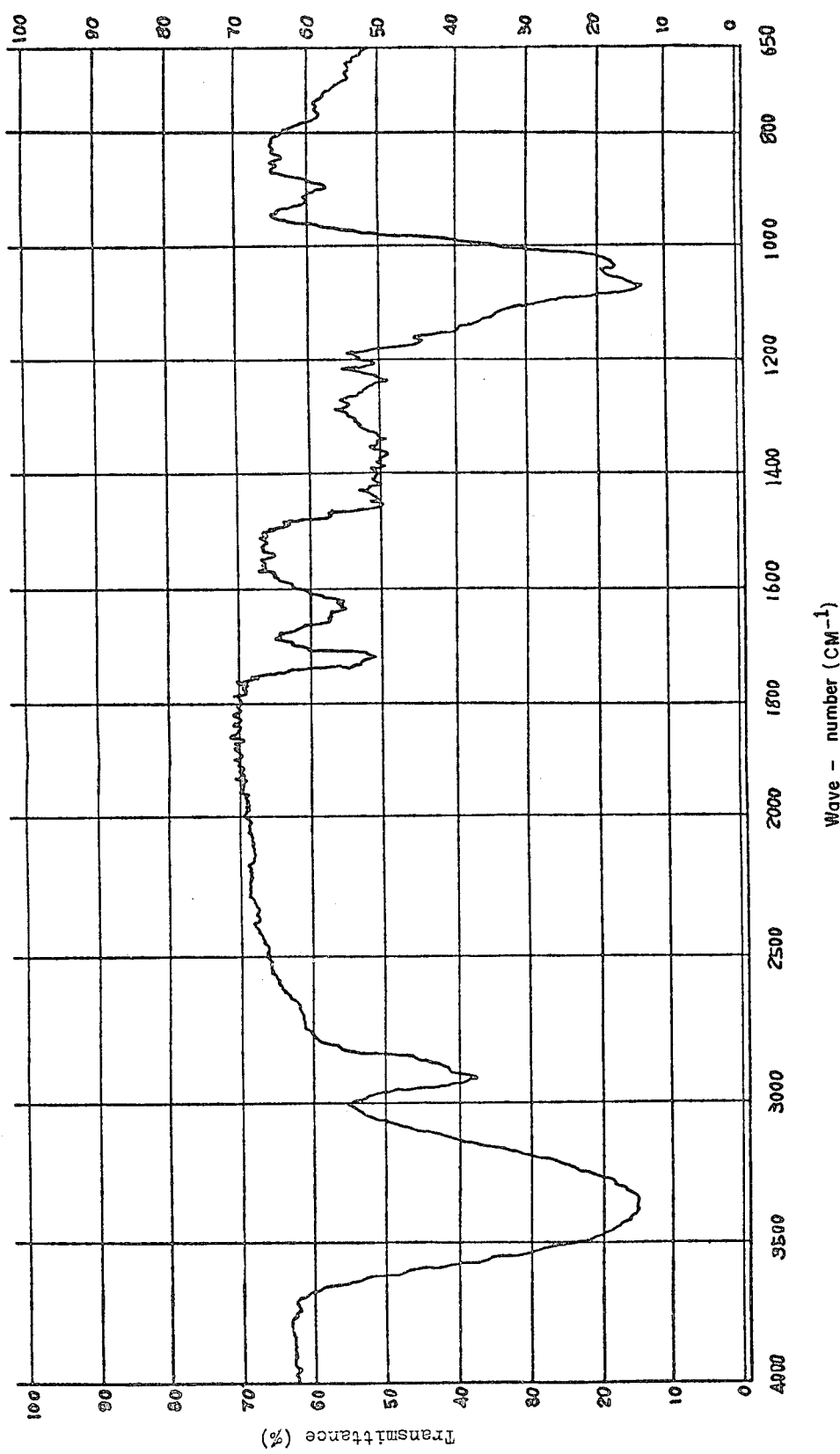

Portions of Samples No. 2 and No. 3 prepared in Experiment 1-(2) were transferred into test tubes, allowed standing in a room maintained at 4° C. for 15 days and compared on their water solubility. As apparent from FIG. 1 wherein the results are given, Sample No. 2 crystallized and became white turbid, whereas Sample No. 3 of the invention remained transparent and had a remarkably improved water solubility.

ing funnel, and alpha-glucosyl sugar compounds and glycosides present in Sample No. 4 were extracted, portioned with the solvent system, and the n-butanol layer was collected. After drying the obtained solid under reduced pressure to remove n-butanol, the dried product was dissolved in a small amount of methanol, then added excess ethyl ether, and the formed precipitate was collected, dried under reduced pressure, and pulverized, whereby 500 mg of powder product (Sample No. 5) was obtained. Sample No. 5 dissolved very easily in water, and was a odorless, white-colored and neutral substance that had a mild, soft, round and pleasant sweetness. It also dissolved partially in lower alcohols such as methanol, ethanol and n-butanol, but was difficultly soluble in chloroform and ethyl ether. The infrared spectrum of Sample No. 5 by the KBr tablet method is shown in FIG. 2. Also its ultraviolet spectrum was investigated, but no characteristic absorbance spectrum was noted.

Figure 3:
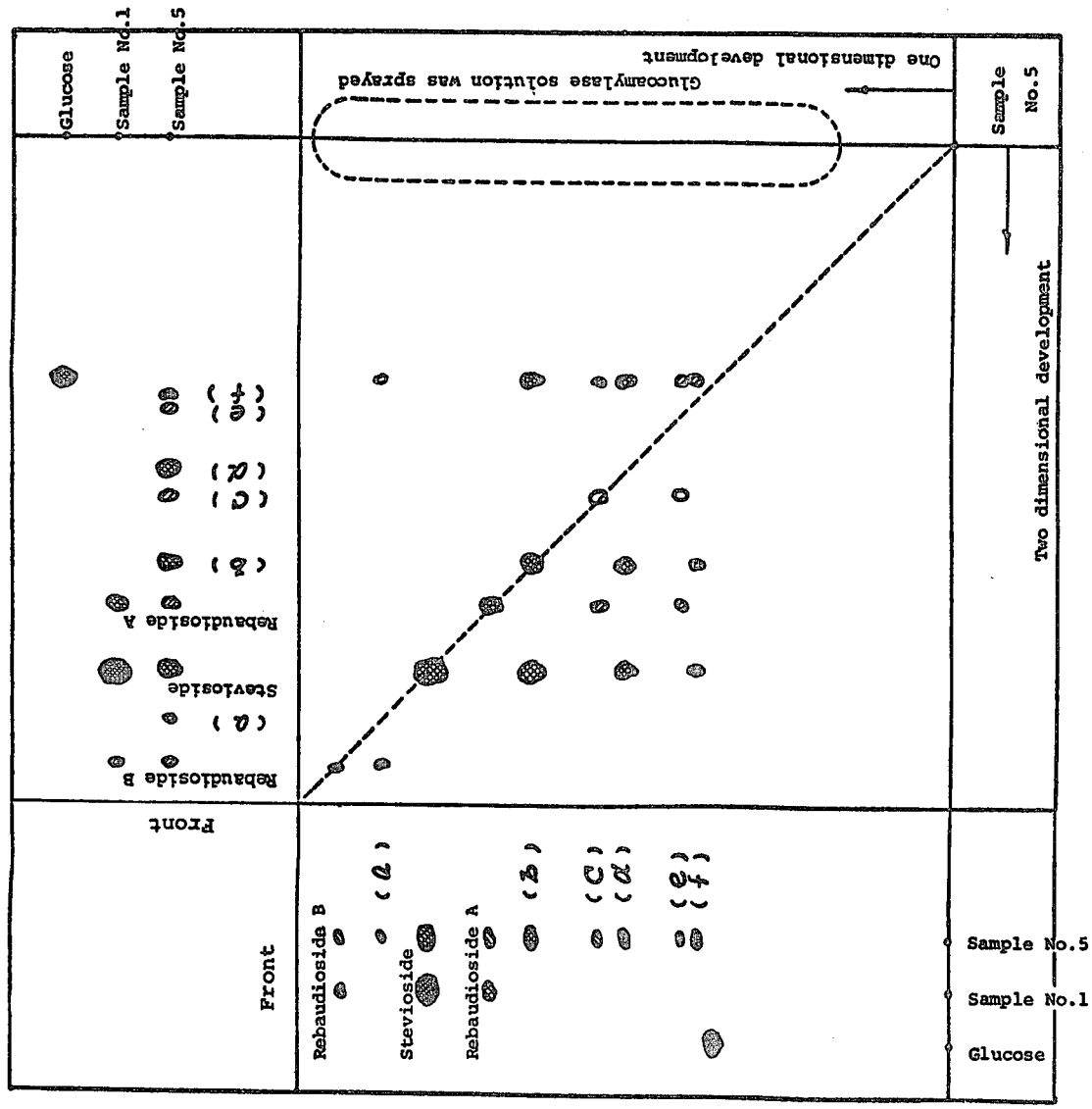

An aqueous solution prepared by dissolving a portion of Sample No. 5 in a small amount of water, an aqueous solution of Sample No. 1 purified similarly as in the case of Sample No. 5 and a solution of D-glucose as a control were spotted on a thin layer plate of Silica gel 60 (Merck & Co., Inc., New Jersey, U.S.A.), and one dimensional development was carried out in a solvent system of chloroform, methanol and water (30:20:4). Then the thin layer plate was air-dried sufficiently. A 0.1 M acetate buffer solution, pH 4.8, in which commercialized crystalline glucoamylase was dissolved, was sprayed on the thin layer plate and then the plate was allowed to stand at 50° C. for two hours taking precaution to prevent drying. Thereafter the plate was air-dried sufficiently and two dimensional development of the plate was carried out using the same solvent system. After drying, the plate was sprayed with a methanol solution containing 50% sulfuric acid, heated and developed. FIG. 3 shows the chromatogram. As FIG. 3 shows, in addition to stevioside spot (Rs 1.00), small spots of rebaudioside A spot (Rs 0.88) and rebaudioside B spot (Rs 1.17) were confirmed by the result of one dimensional development of Sample No. 1 as a control. Whereas the result of the chromatograph Sample No. 5 shows that, besides spots of stevioside and rebaudiosides, new six spots of substances, in the decreasing order of Rs value, i.e., Rs 1.09, Rs 0.80, Rs 0.67, Rs 0.62, Rs 0.51 and Rs 0.48, were developed, which were designated as (a), (b), (c), (d), (e) and (f) respectively.

The result of two dimensional development obtained wherein glucoamylase was allowed to act on Sample No. 5 revealed that spot (Rs 1.17) of rebaudioside B and spot (Rs 0.45) of D-glucose originated from substance (a); spot (Rs 1.00) of stevioside and spot (Rs 0.45) of D-glucose, from substance (b); spot of substance (b), in addition to spot (Rs 1.00) of stevioside and spot (Rs 0.45) of D-glucose, from substance (d); spot of substance (b), in addition to spot (Rs 1.00) of stevioside and spot (Rs 0.45) of D-glucose, from substance (f). Similarly, spot (Rs 0.88) of rebaudioside A and spot (Rs 0.45) of D-glucose originated from substance (c), spot of substance (c), in addition to spot (Rs 0.88) of rebaudioside A and spot (Rs 0.45) of D-glucose, from substance (e).

It is apparent from the results that substances (a)–(f) were decomposed respectively by the action of glycoamylase into D-glucose derivatives of stevioside or rebaudioside, and finally into D-glucose and stevioside, or D-glucose and rebaudioside. Therefore substance (a) was concluded as being a substance in which D-glucose was alpha-linked with rebaudioside B, and substances (b), (d) and (f) as being substances in which one mole of stevioside was also alpha-linked with one or more moles of D-glucose. In other words, the spots were concluded as those of alpha-monoglucosyl stevioside, alpha-diglucosyl stevioside and alpha-triglucosyl stevioside, respectively. Similarly, substances (c) and (e) were concluded as those of alpha-monoglycosyl rebaudioside A and alpha-diglucosyl rebaudioside A, respectively.

Substances (a)–(f) decomposed into stevioside and D-glucose, or rebaudioside and D-glucose when a partially purified alpha-glucosidase extracted from pig liver was allowed to react similarly on them. Substance (f) was found being easily decomposable into substance (b) and maltose by the action of commercialized crystalline beta-amylase.

From these results, substances newly formed by the action of alpha-glucosyltransferase were concluded as being substances in which one mole of stevioside was alpha-linked with one or more moles of D-glucose, or in which one mole of rebaudioside was alpha-linked with one or more moles of D-glucose. This suggested that these substances may be decomposable into stevioside or rebaudioside in vivo in human or animals.

Figure 4:
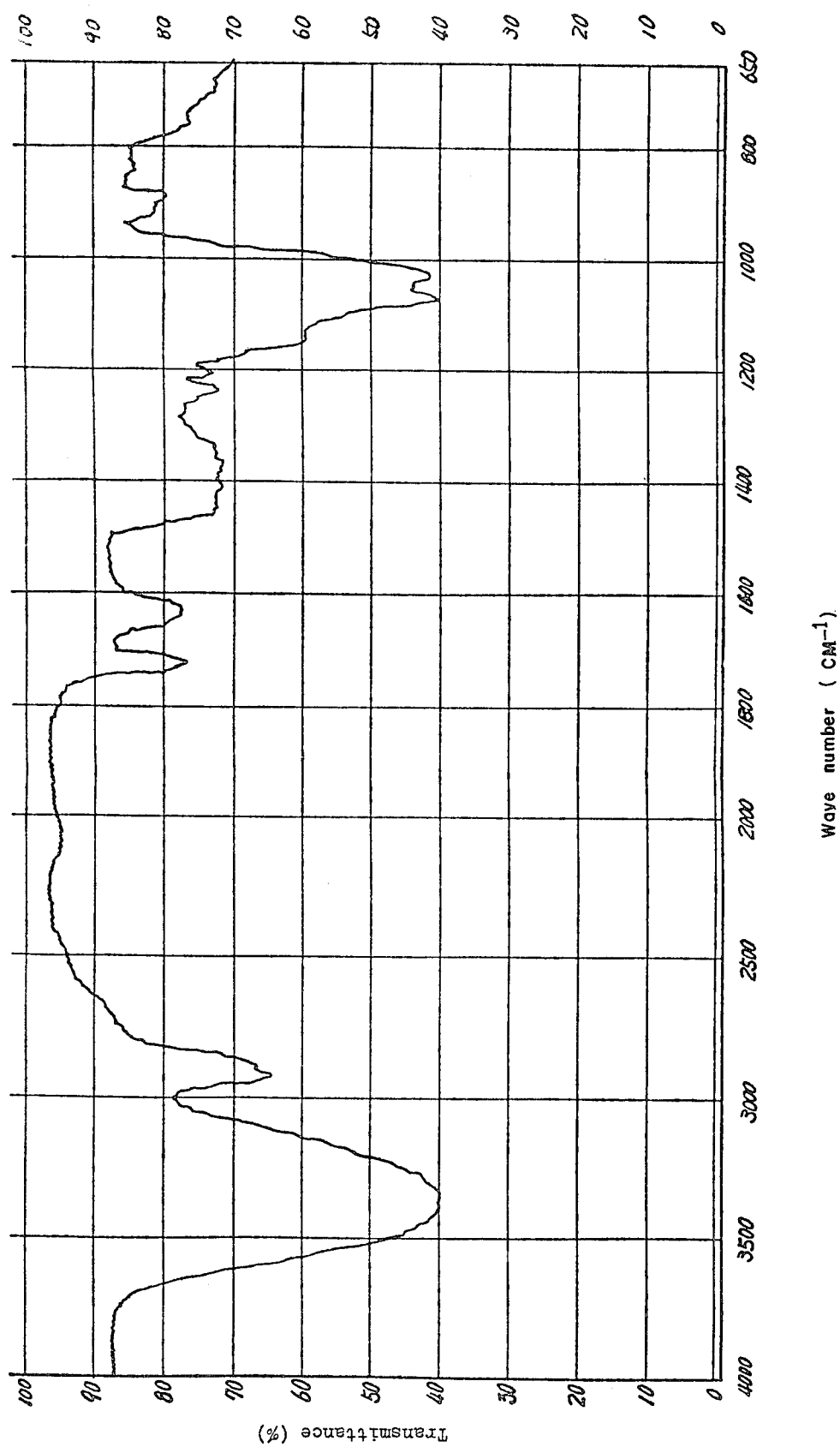

A sample prepared similarly as Sample No. 5 was applied to silica gel column chromatography using solvent system of chloroform, methanol and water (60:30:5) to isolate substance (b), which was then dried to powder. The substance was an extremely readily watersoluble, odorless and white colored sweetener with a mild, soft, but intense sweetness and a pH value around neutrality. It was partially soluble in lower alcohols such as methanol, ethanol and n-butanol, but difficulty soluble in chloroform and ethyl ether. The infrared spectrum of substance (b) by KBr tablet method is shown in FIG. 4.

Since Sample No. 5, one embodiment of the invention, possesses an excellent sweetness, free of a lingering taste and is extremely readily water soluble, similarly as Samples No. 3 and No. 4 employed in the Experiment 2-(2), the purposes of the invention which is to eliminate the disadvantages of stevioside, can be achieved by allowing alpha-glucosyltransferase to react on an aqueous solution containing stevioside and alpha-glucosyl sugar compound to form alpha-glycosyl stevioside.

The invention will be illustrated further with reference to some examples.

EXAMPLE 1

Five liters of a sterilized culture medium containing 4% (w/v) maltose, 0.1% (w/v) potassium dihydrogen phosphate, 0.1% (w/v) ammonium nitrate, 0.05% (w/v) magnesium sulfate.$7H_2O$, 0.05% (w/v) potassium chloride, 0.2% (w/v) polypeptone and 1% (w/v) calcium carbonate which was separately dry heat sterilized and added aseptically to the medium on inoculation was inoculated with a strain of *Mucor javanicus* IFO 4570 and incubated at a temperature of 30° C. for 44 hours with aeration and stirring. After 480 g of the wet myceria obtained from the culture broth was added to M/2 acetate buffer solution pH 5.3 in a 4 M urea 5 liters, the resulting mixture was allowed standing at a temperature of 30° C. for 30 hours. The supernatant of the mixture was dialyzed overnight against running tap water, saturated to 0.9 ammonium sulfate, allowed standing at a temperature of 4° C. overnight, then the precipitates were collected by centrifuge. After suspending the precipitate in 100 ml of acetate buffer, pH 6.0, the mixture was centrifuged and the supernatant was used as alpha-glucosidase (E.C.3.2.1.20).

"Commercialized stevioside" 15 g and maltodextrin, D.E.40, 300 g were dissolved in one liter of heated water, and the mixture solution was cooled to 50° C., added the above alpha-glucosidase solution and allowed standing at pH 6.0 and 50° C. for 24 hours. The reaction solution was heated to inactivate the enzyme therein and then filtered. The filtrate was desalted by passages through ion exchange resins, Amberlite IR-120B (H Type) and Amberlite IRA-94 (OH Type) (Rohm & Haas Co., Philadelphia, U.S.A.), and was concentrated under reduced pressure. The resulting solution was a liquid sweetener with a water content of 30% (w/w). The yield of the liquid sweetener was 97%, d.s.b., against material. The sweetener was about two times sweet as sucrose, d.s.b., free of a lingering taste. Therefore, it can be freely used in sweetening various foods, drinks and confectioneries.

Particularly it can be used as a low cariogenic sweetener bacause oral cariogenic microorganisms do not convert it into a water insoluble glucan.

EXAMPLE 2

A strain of *Bacillus megaterium* FERM-P No. 935 was inoculated on 5 liters of the culture medium of Experiment 1-(1), and the mixture was incubated at 28° C. for three days with aeration and stirring. After the incubation was finished, the resulting culture broth was centrifuged, and the supernatant was salted-out with 0.7 saturation ammonium sulfate and then centrifuged, whereby a precipitate was obtained.

The precipitate contained 300,000 units of cyclodextrin glucanotransferase (E.C.2.4.1.19) as assayed by the method of measurement described in Experiment 1-(1). To a 30% (w/w) sweet potato starch slurry, pH 6.0, was added commercialized liquefying enzyme, 0.2% per dry solid of starch, and the mixture was liquefied continuously at 85°-95° C. The decomposition of the mixture was effected at 80° C. to a D.E.20, and the liquefying enzyme was inactivated by heating. "Commercialized stevioside" was dissolved in the liquefied starch, to give a mixture of one part of "commercialized stevioside" and three parts of partial starch hydrolyzate, d.s.b. The mixture was cooled to 50° C., added cyclodextrin glucanotransferase, 10 units per gram starch, and incubated at 50° C. and pH 6.0 for 48 hours. After inactivating the enzyme in the reaction mixture by heating, the resultant was purified similarly as in Example 1, concentrated under reduced pressure, dried and pulverized, whereby a powder sweetener was obtained in a yield of about 95%, d.s.b. Since the sweetener was low hygroscopic, it was easy to handle. But its water solubility was so high, and it dissolved easily in cold water and even at high concentration easily to form paste.

The sweetener was about 15 times sweet as sucrose, d.s.b., and it possessed a mild, soft, round and pleasant sweetness, free of a lingering taste. The sweetener can be also used whenever sweetening is necessary, but especially, it is suitable as a dental caries preventive and low calorie sweetener.

EXAMPLE 3

Potato starch 300 g and "commercialized stevioside" 100 g were added to one liter of water, and the mixture was added commercialized bacterial saccharifying alpha-amylase (E.C.3.2.1.1) (Seikagaku Kogyo Co., Ltd., Tokyo, Japan), in the amount of 10 units, as assayed by the method of Experiment 1-(1), per gram starch and heated with stirring to 80° C. After finishing liquefaction of the starch, the mixture was cooled to 60° C. and allowed standing for two days. After inactivating the alpha-amylase present in the resulting mixture by heating, the mixture was purified in the same manner as in Example 1, concentrated under reduced pressure, dried and pulverized, whereby a powder sweetener was obtained in a yield of about 95%, d.s.b.

The sweetener has similar qualities as those of the sweetener obtained in Example 2, and also it can be directed to various uses.

EXAMPLE 4

A liquefied starch solution, 30% (w/w) and D.E.15, was prepared by the same method as in Example 2. Into the liquefied starch, was added and dissolved "commercialized stevioside" and sucrose of a third mounts of material starch, respectively, and then added 2 units of cyclodextrin glucanotransferase (E.C.2.4.1. 19) per gram starch, d.s.b., and the mixture was subjected to reaction at 60° C. for 24 hours. After inactivating the enzyme by heating, the resulting mixture was purified by the method in Experiment 1-(2), concentrated and dried, whereby a powder sweetener was obtained.

The sweetener was a mixture containing alpha-glycosyl stevioside, alpha-glycosyl sucrose, etc., wherein the tastes of these compounds were well harmonized and exhibited an excellent sweetness quality. The sweetener was about 15 times sweet as sucrose. It may be used as a sweetener for many uses. Especially, since the reducing power of the sweetener is low, it is a suitable sweetener for products containing amino acids and protein such as sweetening foods, drinks, confectioneries and pickles which undergo heating during production. Since the sweetener is hardly converted into water insoluble glucan by oral cariogenic microorganisms, it is a suitable low cariogenic sweetener for foods and drinks.

EXAMPLE 5

The same reaction as described in Experiment 1-(2) was carried out except using a greenish ocher colored crude stevioside, STV-B, (Ikeda Tohka Industries Co., Ltd., Fukuyama, Japan) containing only about 50% stevioside instead of "commercialized stevioside".

It was found that the sweetener had a remarkably more improved sweetness quality than that of the sweetener obtained by using purified stevioside. The sweetener was analyzed. A large amounts of alpha-glycosyl rebaudioside A and alpha-glycosyl rebaudioside B were detected besides alpha-glycosyl stevioside.

The sweetener is about 10 times sweet as sucrose, and can be used in sweetening various foods, drinks, confectioneries and pharmaceuticals.

In the production of the sweetener, elimination of colors of the starting material presents some difficulties, but may be used advantageously in products such as soy sauce, pickles or salted vegetables, preserved foods boiled down in soy sauce wherein coloring is not so important because it uses as starting material crude stevioside which can be produced at a cheaper cost and in a larger amount than purified stevioside.

EXAMPLE 6

One percent seed culture of *Leuconostoc mecenteroides* IAM 1151 was inoculated on 10 liters of a culture medium containing 4% (w/v) sucrose, 0.5% (w/v) yeast extract, 0.8% (w/v) potassium hydrogen phosphate, 2.4% (w/v) dipotassium hydrogen phosphate, 0.02% (w/v) magnesium sulfate 7H$_2$O and 0.5% (w/v) purified stevioside, and the mixture was subjected to stationary culture at 25° C. for 24 hours. The resulting culture broth was centrifuged and the supernatant was purified similarly as the reaction solution in Example 1, and concentrated, whereby a liquid sweetener, water content 30%, was obtained in a yield of about 60%.

The sweetener possessed a mild, soft, round and pleasant sweetness which was about 20 times sweet as that of sucrose and did not effect crystallization of stevioside. Since the sweetener is highly viscous, it imparts a sweetness and a desirable viscosity to products wherein it is used. It is advantageous for sweetening, e.g., juice, syrup, liquor and pickles or salted vegetables.

Further, the above seed culture was inoculated on the same culture medium as above, but from which purified stevioside was removed, and the mixture was incubated similarly. The thus obtained culture broth was centrifuged, and the supernatant was added calcium phosphate gel. Then the mixture was dialized against tap water, and the dialized solution was centrifuged again to recover the calcium phosphate gel. The dextran sucrase (E.C.2. 4.1.5) solution 100 ml obtained from eluting and concentrating a suspension of the gel in a 0.2 M sodium dihydrogen phosphate solution saturated to 0.35 ammonium sulfate was allowed to react on 5 liters of a solution containing 4% (w/v) sucrose and 0.5% (w/v) purified stevioside at pH 5.3 and 30° C. for 10 hours. After inactivation by heating, the reaction solution was purified, and concentrated in the same manner described above, whereby a liquid sweetener was obtained in a yield of about 90%, d.s.b. Since the alpha-glycosyl stevioside content in the sweetener was decomposed by isomaltodextranase (E.C.3.2.1.94) into isomaltose, stevioside and alpha-monoglucosyl stevioside, it was concluded that the sweetener was a mixture in which one mole of stevioside was alpha-linked with one or more moles of D-glucose.

EXAMPLE 7

A liquid sweetener prepared by dissolving the powder sweetener 26 g obtained in Example 2 in 1 kg of Malbit (food grade maltitol syrup, water content 25%, Hayashibara Co., Ltd., Okayama, Japan) had an excellent sweetness quality, and the sweetness was equal to that of sucrose and the caloric value of the sweetener was about one twentieth of that of sucrose.

The sweetener is suitable for preparing low calorie foods, drinks and confectioneries for those whose caloric intakes are restricted, e.g., the obeses, the diabetics, figure-conscious and weight watchers, and it can be also freely used intact as a table syrup. Since neither acid nor water insoluble glucan is produced by oral cariogenic microorganisms, it is suitable for preparing low cariogenic foods and drinks.

EXAMPLE 8

Glucose 960 g, sucrose 20 g and the powder sweetener 20 g prepared in Example 3 were mixed uniformly, and the mixture was pulverized into a powder sweetener.

Its sweetness was roughly equal to that of sucrose and its sweetener quality was excellent. Further, the sweetener was soluble in cold water.

A chilled aqueous solution of the sweetener itself may be used as a delicious soft drinks. It was concluded that the excellent sweetness quality of the powder sweetener mixture is due to the synergic effect of the above three constituents, i.e., glucose, sucrose and power sweetener.

EXAMPLE 9

A complex sweetener was prepared by dissolving 100 g of powder sweetener Sample No. 4 obtained in Experiment 1-(2) in 20 ml of water and by admixing uniformly 1 kg of honey thereto.

The sweetener was about two times sweet as sucrose and its sweetness quality was very excellent. Further the presence of Sample No. 4 intensified fragrance of honey. It can be freely used as a sweetener for beauty drinks, health diets and the likes as well as a taste improver for herb medicines.

What we claim is:

1. A process for producing a sweetener containing alpha-glycosyl stevioside comprising allowing alpha-glucosyltransferase to react on an aqueous solution containing stevioside and alpha-glucosyl sugar compound for a time sufficient to produce said alpha-glucosyl stevioside.

2. A process for producing sweetener according to claim 1 wherein said alpha-glucosyltransferase is a member or members selected from the group consisting of alpha-glucosidase, alpha-amylase, cyclodextrin glucanotransferase, dextransucrase, dextrindextranase and amylosucrase.

3. A process for producing sweetener according to claim 1 wherein said alpha-glucosyl sugar compound is a member or members selected from the group consisting of maltooligosaccharide, starch, partial starch hydrolyzate and sucrose.

4. A process for producing sweetener according to claim 1 wherein said sweetener is a low caloric sweetener.

5. A process for producing sweetener according to claim 1 wherein said sweetener is a low cariogenic sweetener.

* * * * *